United States Patent [19]

Haber et al.

[11] 4,070,469
[45] Jan. 24, 1978

[54] COMPOUND FOR THE TREATMENT OF BOVINE MASTITIS

[75] Inventors: Raphael Ralph G. Haber; Eva Schöenberger, both of Givatayim; Morris E. Stolar, Tel-Aviv, all of Israel

[73] Assignee: Abic Ltd., Israel

[21] Appl. No.: 700,173

[22] Filed: June 28, 1976

[30] Foreign Application Priority Data

July 3, 1975 Israel .......................................... 47633

[51] Int. Cl.$^2$ .............................................. A61K 31/47
[52] U.S. Cl. .................................................. 424/258
[58] Field of Search ..................... 260/287 G; 424/258

[56] References Cited

PUBLICATIONS

Haber – Chem. Abst., vol, 71, (1969), p. 91337v.

Primary Examiner—Sam Rosen
Attorney, Agent, or Firm—Steinberg & Blake

[57] ABSTRACT

Compositions for the treatment of bovine mastitis are provided. Said compositions comprise as active compound [2-carboxy-4-/2'-(5'-nitrofuryl)]quinoline N-oxide. The method is performed in such a manner that the composition is administered to the animal, preferably by way of intramamary infusion.

9 Claims, 1 Drawing Figure

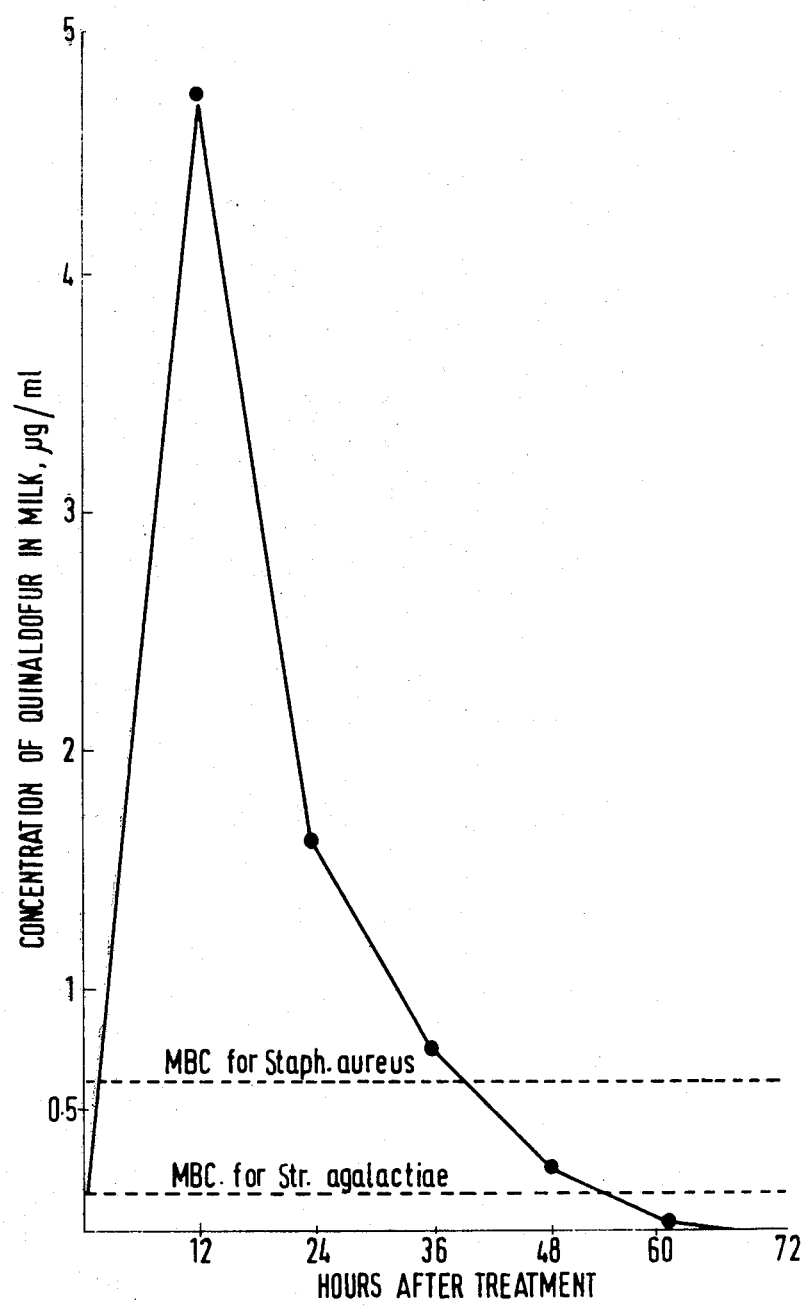

COMPOUND FOR THE TREATMENT OF BOVINE MASTITIS

The present invention relates to a method for the treatment of bovine mastitis and to compositions for the performance of such method.

Bovine mastitis is an infection of the udder of ruminants such as cows, mainly caused by gram positive bacteria and especially prevailing in cows in intensive milk products units. The main reason for this disease is the transfer of infection from one animal to the other during the milking process. The main pathogens causing bovine mastitis are *Staphylococens aur., Strep. agalactiae, Strep.dyagalactiae* and *Strep.uberis*.

Compounds or compositions comprising said compounds used in the treatment of bovine mastitis should give the following results;

1. Most or all of the above pathogens should be in the presence of milk and other udder fluids susceptible to the active compound.
2. The therapeutic effect should be relatively quick
3. No significant irritation should be caused to the udder of the cow, by either the active or other ingredients of composition
4. The active compound should not stay in the milk for a period much in excess of the one required for therapeutic activity so as to minimise the loss of milk, which has to be discarded as long as a foreign compound is present.

There are other requirement for such a composition for the treatment of mastitis but the above four criteria are the most important ones.

Bovine mastitis has so far be treated mainly by administering anti-infective agents such as antibiotics, e.g. Penicillin G, Dihydrosteptromycin, etc.; sulfonamides or other chemotherapheutically active compounds or of a composition comprising such an active compound into the udder. Such treatment can also be seconded by the addition of an anti-inflammatory agent to take care of secondary symptoms, e.g. the inflammation due to the infection.

However, none of the above compounds utilised so far has been entirely satisfactory, as will be shown later on. Additionally it has been found to be very desirable to replace antibiotica by chemo-therapeutical drugs, inter alia, for the following reasons:

1. Antibiotica effective in human medicine should not be utilised in veterinary medicine, in order not to build up a strain resistance against bacteria appearing in human diseases.
2. Antibiotica should be reserved for such diseases for which no chemo-therapeutical drug would be available, as it has been proved that strains build up after extended use as a resistance against the antibiotica used.
3. Staph.aur., one of the above pathogens, has already built up a resistance against most of the antibiotica utilised in the treatment of bovine mastitis. It has thus been very important to find a method for the treatment of bovine mastitis utilising a composition comprising as active compound one which substantially would overcome the drawbacks of the compound utilised so far and would give the desired results as set out above.

In Israel Patent Specification No. 26,022 there have been disclosed and claimed nitrofuryl quinoline derivatives bearing in either the 2- or 4-position a 5-nitrofuryl group which quinoline derivative may be further substituted by one or more substituents selected among the group consisting of lower alkyl ($C_1$–$C_5$)radicals; lower alkyl radicals substituted by halogen and/or hydroxy; lower alkoxy($C_1$–$C_5$)radicals, carboxylic acyloxy, carboxylic acyloxy methyl and nitro groups; halogen atoms, amino groups; amino groups substituted by carboxylic acyl and/or alkyl groups; cycloalkyl radicals; carboxy groups and their esters and amides and, if desired, the carbon atoms in the 6 and 7 position being part of a further benzene nucleus and their nitrogen oxides, and non-toxic acid-addition salts, and compositions comprising said compounds. Said compounds have excellent antibacterial properties against gram positive bacteria.

The activity of some of said nitrofuryl quinolines derivatives against Strep.uberis and Stap.Aureus in milk has been compared with the activity of some of the compounds so far utilised in the treatment of bovine mastitis. The results are shown in Table I. (The nitrofuryl quinoline derivatives have general formula

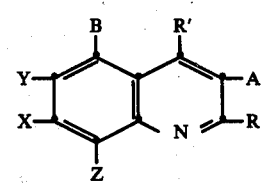

the meaning of R, A, R', B, Y, X and Z being given in the Table. $R_1=O$ whenever indicated then the N-oxide is concerned; NF stands for nitrofuryl)

Table I

Minimal Bactericidal/Activity (MBC) of representative Nitrofuryl quinolin in mcg/ml in milk at pH 7.2 – 7.4. Versus Standards (Field isolates)

| | | | | | | | | | Strep.urberis | | Staph.Aureus | |
|---|---|---|---|---|---|---|---|---|---|---|---|---|
| No. | $R_1$ | R | A | R' | B | Y | X | Z | 127A | 60B | 2372 | 2337 |
| 1 | O | COOH | H | NF | H | H | H | H | 0.25 | 0.015 | 0.25 | 0.5 |
| 2 | | COOH | H | NF | H | H | H | H | 1 | 0.12 | 0.5 | 1 |
| 3 | | NF | H | H | H | H | H | H | >10 | >10 | >10 | >10 |
| 4 | O | NF | H | $CH_3$ | H | H | H | H | >10 | >10 | >10 | 10 |
| 5 | | $CH_3$ | H | NF | H | H | H | H | 10 | 10 | >10 | >10 |
| 6 | O | $CH_3$ | H | NF | H | H | H | H | 5 | 5 | 5 | 5 |
| 7 | | $CH_3$ | H | NF | H | $O_2H_5$ | H | H | >10 | >10 | >10 | >10 |
| 8 | | $CH_3$ | H | NF | H | H | $OCOCH_3$ | H | 10 | 0.25 | 5 | 5 |
| 9 | | $CH_3$ | H | NF | H | H | $OCH_3$ | H | 5 | 10 | 5 | 5 |
| 10 | | $CH_3$ | H | NF | H | H | H | $C_2H_5$ | >10 | >10 | >10 | >10 |
| 11 | | H | H | NF | H | H | H | H | >10 | 10 | >10 | >10 |
| 12 | | $C_2H_5$ | H | NF | H | $CH_3$ | H | H | >10 | >10 | >10 | >10 |
| 13 | | $CH_2OH$ | H | NF | H | H | H | H | >10 | 5 | 5 | 10 |
| 14 | | $CBr_3$ | H | NF | H | H | H | H | 5 | 5 | >10 | 10 |
| 15 | | CH=NOH | H | NF | H | H | H | H | 1 | 1 | 1 | 1 |
| 16 | | CH=NOH | H | NF | H | H | $OC_2H_5$ | H | 10 | 5 | 5 | 10 |
| 17 | | COOH | H | NF | H | H | $OC_2H_5$ | H | 1 | 0.03 | 0.5 | 1 |

Table I-continued

Minimal Bactericidal/Activity (MBC) of representative Nitrofuryl quinolin in mcg/ml in milk at pH 7.2 – 7.4. Versus Standards (Field isolates)

| | | | | | | | | | Strep.urberis | | Staph.Aureus | |
|---|---|---|---|---|---|---|---|---|---|---|---|---|
| No. | R₁ | R | A | R' | B | Y | X | Z | 127A | 60B | 2372 | 2337 |
| 18 | | CON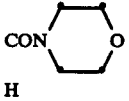O | H | NF | H | H | H | H | >10 | 5 | 10 | >10 |
| 19 | O | H | H | NF | H | H | OCH₃ | H | 0.5 | 0.12 | 0.5 | 0.5 |
| 20 | O | CH₃ | H | NF | H | C₂H₅ | H | H | >10 | >10 | 5 | 5 |
| 21 | O | CH₃ | H | NF | H | H | CH₃ | H | 10 | 5 | 10 | 5 |
| 22 | O | CH₃ | H | NF | H | H | OH | H | 0.5 | 0.12 | 0.5 | 1 |
| 23 | O | CH₃ | H | NF | H | H | OCH₃ | H | 5 | 5 | 5 | 5 |
| 24 | O | C₂H₅ | H | NF | H | H | OCH₃ | H | >10 | >10 | 10 | >10 |
| 25 | O | COOH | H | NF | H | H | OCH₃ | H | 0.5 | 0.25 | 5 | 1 |
| 26 | O | COOH | H | NF | H | H | OC₂H₅ | H | 1 | 0.03 | 1 | 1 |
| 27 | | CH₃ | H | NF | H | CH₃ | H | H | 10 | 10 | 10 | 10 |
| 28 | | CH₃ | H | NF | H | H | Cl | H | >10 | >10 | >10 | >10 |
| 29 | O | CH₃ | H | NF | H | CH₃ | H | H | 5 | 5 | 5 | 5 |
| 30 | O | C₂H₅ | H | NF | H | H | H | H | >10 | 5 | 10 | 5 |
| 31 | | C₂H₅ | H | NF | H | C₂H₅ | H | H | >10 | >10 | >10 | >10 |
| 32 | O | C₂H₅ | H | NF | H | C₂H₅ | H | H | >10 | 1 | >10 | >10 |
| 33 | | CH₂OAC | H | NF | H | H | H | H | >10 | >10 | >10 | >10 |
| 34 | | CH₃ | H | NF | H | NH₂ | OCH₃ | H | 1 | 0.25 | 5 | 5 |
| 35 | | CH₃ | H | NF | H | H | NH₂ | CH₃ | 10 | 5 | 5 | 5 |
| 36 | | CH₃=N—NH, CH₃ | H | NF | H | H | H | H | 5 | 5 | 5 | >10 |
| 37 | | CH₃ | H | NF | H | OCH₃ | OCH₃ | H | 10 | 5 | 5 | 10 |
| 38 | | CH=NOH | H | NF | H | H | OC₂H₅ | H | 10 | 5 | 5 | 10 |
| 39 | O | CH₃ | H | NF | H | OCH₃ | OCH₃ | H | 1 | 0.25 | 0.5 | 10 |
| 40 | O | C₂H₅ | H | NF | H | CH | CH₃ | H | 10 | 5 | 5 | 5 |
| 41 | O | H | H | NF | H | H | H | H | 10 | 5 | 5 | 10 |
| 42 | O | CH₃ | H | NF | H | H | OC₃H₇ | H | 5 | 5 | 5 | 10 |
| Furazolidone | | | | | | | | | >10 | 10 | >10 | >10 |
| Furaltadone | | | | | | | | | >10 | 1 | 10 | 10 |
| Penicillin G | | | | | | | | | 1.56 | 0.06 | >50 | >50 |
| Oxytetracyclin | | | | | | | | | >50 | 0.78 | 50 | 25 |
| Kanamycin | | | | | | | | | 100 | 100 | 12.5 | 12.5 |
| Erythremycin | | | | | | | | | 3.12 | 0.39 | 6.25 | 0.78 |
| Spiramycin | | | | | | | | | 12.5 | 1.56 | 25 | 25 |
| Chloramphenicol | | | | | | | | | >400 | 50 | >50 | >50 |
| Rifamycin | | | | | | | | | >50 | 3.12 | 0.12 | 0.12 |
| Necmycin | | | | | | | | | 200 | 200 | 12.5 | 12.5 |

The above results indicate that most of the above nitrofuryl quinoline derivatives lost their activity against the above bacteria to a large extent when being tested in the presence of milk. Only compounds 1, 19, 22 and 26 showed significant activity in milk against said bovine mastitis. Compounds 1, being 2-carboxy-4-[2'-(5'-nitrofuryl)]quinoline N-oxide(hereinafter called 4-(5-nitrofuryl-quinaldinic acid)N-oxide being the most active one.

Said four compounds were then tested for the length of time they could be detected in the milk of the cow. For this purpose 500 mg in 7 ml of a polyethylene glycol (P.E.G.) base of each compound were administered to several cows and the residue of active compound in milk were measured in mcg/ml after 24, 32 and 40 hours respectively. The results are shown in Table II

Table II

| Compound | 24 hrs. | 32 hrs. | 40 hrs. |
|---|---|---|---|
| 1 | 9.8 | — | — |
| 22 | 20.0 | — | — |
| 19 | 26.5 | 5.0 | — |
| 26 | 12.0 | 5.0 | — |

The above results indicate that the 4-(5-nitrofuryl)-quinaldinic acid N-oxide remained the shortest time in the milk.

Thereafter 500 mg of each of said compounds in 7 ml of a P.E.G. base and also 7 ml of said base above were administered to several cows and the number of leucocytes (sematic cells) in 10⁶ per ml of milk were measured before administration and 40, 48 and 56 hours thereafter. The numbers of leucocytes present indicate the degree of irritation of the udder. The results are shown in Table III

Table III

| Compound | Before | 40 hrs. | 48 hrs. | 56 hrs. |
|---|---|---|---|---|
| 1 | 0.28 | 0.95 | 1.5 | 0.95 |
| 22 | 0.28 | 5 | 5 | 3.15 |
| 19 | 0.60 | 5 | 3 | 2 |
| 26 | 0.22 | >7.5 | 3 | 2.65 |
| P.E.G. base | 0.57 | 5 | 1.42 | 1.0 |

The above results indicate that the 4-(5-nitrofuryl) quinaldinic acid N-oxide caused the lowest irritation.

The above results, namely the good microbiological activity in milk (Table I), the relative quick disappearance from the milk (Table II) and the low irritation caused to the udder (Table III) and its non-toxicity (LD$_{50}$mice=3g/kg; LD$_{50}$rats=1.6g/kg indicated that 4-(5-nitrofuryl)-quinaldinic acid N-oxide would be suitable to be utilised in the treatment of bovine mastitis.

This indication was verified by testing in vitro by the method of serial dilution the sensitivity of said compound against udder pathogens in milk in various concentrations measured in meg/ml of milk. The number of strains which were killed at each concentration were measured after 24 hours. The results are given in Table IV Table IV

| Microorganism | No. of Strain | Concentration | | | | | | | | |
|---|---|---|---|---|---|---|---|---|---|---|
| | | 0.02 | 0.04 | 0.08 | 0.16 | 0.31 | 0.62 | 1.25 | 25 | 5 |
| Str.agalactiac | 34 | 5 | 12 | 13 | 1 | 1 | 1 | 1 | — | — |
| Str.dysgalactiae | 18 | 1 | 2 | 13 | 1 | — | 1 | — | — | — |
| Str.uberis | 32 | — | — | — | 1 | 9 | 18 | 2 | 1 | 1 |
| Enterococci | 8 | — | 2 | 3 | 2 | 1 | — | — | — | — |
| Staph.aureus | 86 | — | — | — | 4 | 14 | 51 | 15 | 1 | — |
| C.pyogenes | 3 | — | — | — | — | — | 1 | 2 | — | — |

The present invention thus consists in 4-(5--nitrofuryl)-quinaldinic acid N-oxide to be utilised in the treatment of bovine mastitis.

The present invention consists also in a method for the treatment of bovine mastitis in which 4-(5-nitrofuryl)-quinaldinic acid N-oxide is administered to the udder of the cow suffering from said disease.

Said method is advantageously performed by administering 2-3 doses comprising 50-1000 mg of the active compounds in intervalls of 16 to 48 hours. Preferably said doses comprise 100-500 mg of active compound per dose and said doses are administered about each 24 hours.

In has been shown that said range is effectful by an efficiency test in which various doses of 4-(5-nitrofuryl)-.quinaldinic acid N-oxide were administered to cows suffering from bovine mastitis. There were adminstered 2 doses in intervals of 24 hours. The results are shown in Table V in cured quarters/treated quarters.

Table V

| Dose | Steph.aureus | | Str.dysgal. | | Str.uberls | |
|---|---|---|---|---|---|---|
| 50 mg | 15/30 | 50% | 10/16 | 62.5% | 8/13 | 61.5% |
| 100 mg | 6/8 | 75% | 4/5 | 80% | 4/5 | 80% |
| 250 mg | 6/8 | 75% | 5/6 | 83% | 4/5 | 80% |
| 500 mg | 8/9 | 88% | Not tested | | 5/6 | 84% |

Sometimes, a cow should be treated, as a preventive manner, even if it is not clear whether she suffers from bovine mastitis, i.e. it might be that he rudder is healthy. This is important, for instance, in case that it is clear that some cows of a herd are suffering from bovine mastitis and then one may be interested to treat all cows of said herd in order to ascertain that no further cow should be infected and that also this possibility is within the scope of the present invention.

Moreover, it should be understood that the method according to the present invention may be performed with milking cows as well as with dry cows.

The active compound is preferably administered in the form of a composition by way of intramamary infusion, i.e. the composition is injected into the teat through the milk canal. Thus, the present invention consists also in a composition for the treatment of bovine mastitis comprising as active compound 4-(5-nitrofuryl)quinaldinic acid N-oxide.

In case of dry cows it is desirable that the active compound should stay for a longer time in the udder. This can be achieved by varying the composition, e.g. by the addition of mineral oil.

Said composition is preferably an ointment or cream, but may also have any other suitable form, e.g. solution, suspension, etc.

Various different compositions are suitable for the purpose of the present invention. The most suitable one being a composition comprising per dose a. 50-1000 mg of 4-(5-nitrofuryl)quinaldinic acid;

b. a gelling agent selected from the group of aluminium fatty acid salts in a concentration between 1% to 15%;

c. a vegetable oil or a mineral oil in an amount that the does will be 2-25 g.

In case that a vegetable oil is present there is advantageously added an emulsifier having a hydrophile-lipophile Balance(HLB) between 8-12 in a concentration between 0.1-5% by weight of the dose.

Suitable emulsifiers are, inter alia:

a. Polyoxyethylene-sorbitan-stearates or oleates, e.g. Tween 61, Tween 81 and Tween 85 (See Merck Index, 8th Edition page 972)

b. Polyoxylethylene-sorbitol fatty acid esters c. Polyoxyethylene alcohol fatty acid esters such as lauryl esters, e.g. Brij 35. p The preferred concentration in which said emulsifiers are present is between 0.5-1.5% by weight.

Suitable gelling agents are, for example, aluminium fatty acid salts, e.g. stearates, palmitates and oleates.

The preferred concentration in which said gelling agents are present is 3-6% by weight.

As suitable vegetable oils there may be mentioned, for example, peanut oil(arachis), corn oil, soya bean oil, etc. The preferred vegetable oil is the peanut oil. The preferred amount utilised is 6-12g per dose.

As suitable additional compounds there may be mentioned:

a. an antioxidant, e.g. butylated hydroxy anisol(-BHA), for the protection of the vegetable oil b. a suitable dye colouring the milk. The absence of said dye in the milk indicates that no traces of the composition are still in the milk.

The composition according to the present invention is prepared by methods known per se, i.e. by admixing the various ingredients in conventional equipment. Care has to be taken that good dispersion of the active compound in the entire composition is obtained. This is best achieved using a ball mill or a three roller-mill.

The invention will now be illustrated with reference to the following Examples without being limited by them.

EXAMPLE 1

The reaction vessel is charged with 75 kg of acetic acid and 10 kg of 4-(5-nitrofuryl)-quinaldinic acid(m.p. 205°-207° C).

The resulting slurry is heated to 90°-95° C and 30% of aqueous hydrogen peroxide is added in portions in the course of 6-8 hours. The total amount of hydrogen peroxide 30% added is 96 kg. The N-oxidation reaction is generally completed within 10-12 hours.

Then the reaction mixture is cooled to 20° C, and filtered.

The filter cake is washed with acetic acid and thereafter with methanol.

The compound obtained is dried in an oven at 60° C.

7.4 kg of a yellow, colourless, crystalline powder being 4-(5-nitrofuryl)-quinaldinic acid N-oxide are obtained (m.p. 190° C decomp.).

EXAMPLE 2

A composition comprising the following ingredients was prepared:
1. 4-(5-nitrofuryl)-quinaldinic acid N-oxide 100 mg
2. 9 g of a base comprising:
   a. aluminium stearate: 36 mg
   b. Tween 61: 80 mg
   c. peanut oil B.P.: Till 9 g The mean concentration of the active compound in the milk of 10 cows were measured and the results are given in FIG. 1 of the drawings.

The cure rate obtained by the treatment with said composition is shown in Table VI.

Table VI

| Treatment | Staph.aur. | | Str.sgal. | | Str. dysgal. | | Str.uberis | | Total | |
|---|---|---|---|---|---|---|---|---|---|---|
| 2/24 | 2/4 | 50% | — | — | 1/1 | 100% | 7/8 | 87.5% | 10/13 | 76% |
| 3/24 | 20/25 | 80% | 12/12 | 100% | 2/2 | 100% | 6/7 | 85.7% | 40/46 | 87% |
| 3/16 | 6/7 | 85.7% | 99/103 | 96.1 | — | — | — | — | 105/110 | 95.4% |
| Total | 28/36 | 77.7% | 111/115 | 96.5% | 3/3 | 100% | 13/15 | 86.6% | 155/169 | 97% |

In the column treatment there is indicated the number of treatments/intervall of treatment in hours.

In the result column there are given first numbers of cured quarters/treated quarters and second the success in percentages.

The composition was prepared as follows:

A. Preparation of Base 0.37 Kg of aluminium monostearate was dispersed in 8.55 kg of peanut oil, then the dispersion was gently heated with stirring until the solution reached 150° C.

Stitting was stopped and the solution was left to cool to room temperature. Then 0.08 kg of Tween 61 was warmed until it was clear and then added to the congealed peanut oil. The whole mass was well admixed.

B. Preparation of Final Dosage Form

The base obtained (step A) was added to 100 g of 4-(5-nitrofuryl)quinaldinic acid N-oxide and the mass was diluted geometrically until it was homogeneous. The product was passed through a three roller mill and then remixed. 9.1 g of the product was filled into a plastic disposable syringe.

EXAMPLE 3

The following composition was prepared in the same manner as described in Example 2
4-(5-nitrofuryl)-quinaldinic acid N-oxide: 0.050 g
Peanut oil:1.928 g
Al. stearate: .0195 g
Polyoxyethylene sorbitanstearate: .00195 g

EXAMPLE 4

The following composition was prepared in the same manner as described in Example 2.
4-(5-nitrofuryl)-quinaldinic acid N-oxide: 0.100 g
Soya oil: 19.925 g
Aluminium palmitate: 3.73 g
Polyoxyethylene-(4)sorbitan monostearate: 1.245 g

EXAMPLE 5

The following composition was prepared in the same manner as described in Example 2
4-(5-nitrofuryl)-quinaldinic acid N-oxide: 0.200 g
Sesame oil: 8.513 g
Aluminium stearate: 0.99 g
Polyoxyethylene sorbitolester of tallow: .297 g

EXAMPLE 6

The following composition was prepared in the same manner as described in Example 2:
4-(5-nitrofuryl)-quinaldinic acid N-oxide: 1.00 g
Mineral oil: 14.00 g
Petroleum Jelly: 4.8 g
Aluminium palmitate: 0.2 g This composition is to be utilised for the treatment of dry cows. The retention of the active compound is 16 quarters was tested. It was:
after 5 days: 8.16 μg/ml
after 14 days: 2.27 μg/ml
after 20 days: 0.57 μg/ml

EXAMPLE 7

The following composition was prepared in the same manner as described in Example 3
4-(5-nitrofuryl)-quinaldinic acid N-xoide: 0.25 g
PEG 4000: 0.90 g
Propylene glycol: 2.00 g
PEG 300: 6.85 g

We claim:

1. Composition for the treatment of bovine mastitis, comprising a pharmaceutical carrier suitable for administration in a bovine udder and a bovine mastitis treating effective amount of 2-carboxy-4-[2'-(5'-nitrofuryl)] quinoline N-oxide.

2. Composition according to claim 1 wherein the amount of said compound per unit does is between about 50–1000 mg.

3. Composition according to claim 1 wherein the amount of said compound per unit dose is between about 100 and 500 mg.

4. Method of treating an animal for bovine mastitis, which comprises administering to said animal a bovine mastitis treatment effective amount of 2-carboxy-4-[2'-(5'-nitrofuryl)]quinoline N-oxide.

5. Method according to claim 4 wherein the administration is effected to the udder of the animal.

6. Method according to claim 4 wherein 2–3 doses of 50–1000 mg of said compound are administered to the udder of the cow at intervals of 16 to 48 hours.

7. Method according to claim 4 wherein 100–500 mg of said compound are administered to the udder of the animal at intervals of about 24 hours.

8. Method according to claim 4 for treatment of a dry cow wherein said compound is administered into the udder of the animal in the form of a composition having a long retention time therein.

9. Method according to claim 5 wherein the composition is in the form of an ointment or cream.